United States Patent [19]

Leichnitz et al.

[11] Patent Number: 5,069,879
[45] Date of Patent: Dec. 3, 1991

[54] AUTOMATED APPARATUS FOR DETECTING GASEOUS COMPONENTS IN AIR WITH A COLORIMETRIC TESTING TUBE

[75] Inventors: Kurt Leichnitz, Gross Grönau; Wolfgang May, Reinfeld; Wolfgang Bäther; Wolfgang Evers, both of Lübeck, all of Fed. Rep. of Germany

[73] Assignee: Drägerwerk Aktiengesellschaft, Lübeck, Fed. Rep. of Germany

[21] Appl. No.: 367,325

[22] Filed: Jun. 16, 1989

[30] Foreign Application Priority Data

Jun. 29, 1988 [DE] Fed. Rep. of Germany ....... 3821831

[51] Int. Cl.$^5$ ............................................. G01J 1/50
[52] U.S. Cl. ........................................ 422/86; 422/58; 422/63; 422/87; 422/98; 436/165; 436/902; 364/525; 364/526
[58] Field of Search ................. 422/58, 63, 83, 86, 422/87, 98; 436/165, 902; 364/525, 526

[56] References Cited

U.S. PATENT DOCUMENTS

| | | | |
|---|---|---|---|
| 4,123,227 | 10/1978 | Heim et al. | 427/86 X |
| 4,230,457 | 10/1980 | Leichnitz | 422/86 X |
| 4,245,997 | 1/1981 | Wiesner | 422/86 X |
| 4,777,907 | 10/1988 | Sänger | 198/400 X |
| 4,795,613 | 1/1989 | Azuma et al. | 422/67 X |
| 4,863,694 | 9/1989 | Kimmel et al. | 422/52 X |
| 4,913,881 | 4/1990 | Evers | 422/56 |

Primary Examiner—Robert J. Warden
Assistant Examiner—Laura E. Collins
Attorney, Agent, or Firm—Walter Ottesen

[57] ABSTRACT

The invention is directed to an arrangement for detecting gaseous components in air wherein an air pumping device pumps a sample quantity through the testing tube. The air pumping device includes a receiver for the testing tube and the charge in the testing tube is evaluated. The arrangement is improved in that the detection of different components with the corresponding testing tubes is conducted automatically in that the data characteristic for the measurement is automatically considered and processed to a display of the measured values. For this purpose, the testing tube is provided at its outer periphery with a machine-readable memory whose data is detected by a read unit when the testing tube is introduced into the receiver of the pumping device. The data from the machine-readable memory is conducted to an evaluation unit.

9 Claims, 2 Drawing Sheets

AUTOMATED APPARATUS FOR DETECTING GASEOUS COMPONENTS IN AIR WITH A COLORIMETRIC TESTING TUBE

FIELD OF THE INVENTION

The invention relates to an apparatus for detecting gaseous components in air wherein a sample quantity is pumped through a colorimetric testing tube by means of an air-pumping device. The resulting coloration zone of the indicator is determined by an evaluation unit. An automated measuring method is also disclosed.

BACKGROUND OF THE INVENTION

An apparatus of the kind described above is disclosed in U.S. Pat. No. 4,123,227 incorporated herein by reference. In the gas measuring and warning apparatus disclosed in this patent, a sample quantity of the gas to be detected is passed through the testing tube by means of an air-pumping device. The presence of a specific pollutant to be detected leads to a coloration reaction with the indicator contained in the testing tube. After the sample is taken, the coloration zone is scanned with the aid of a row of mutually adjacent diodes and receivers which define respective light barriers. The length of the coloration zone detected in this manner is applied to an evaluation unit by means of which corresponding measurement values are determined and displayed.

The detection method using colorimetric testing tubes can however not be carried out for all types of pollutants in the same manner. Depending upon the pollutant to be detected, other charges of the testing tube, other indicators, and therewith different sample quantities must be pumped through the testing tube. In addition to these characteristics, not only is the sample quantity to be pumped in accordance with the desired detection sensitivity different, but also the length of the coloration zone is different. In this way, the length of the coloration zone when detecting the one gas corresponds to a specific concentration which, when detecting another gas, can lead to a distinctly different length of the corresponding coloration zone. The individual data characteristic for the testing tube are therefore not available to the evaluation unit so that the display is correct only for a predetermined type of testing tube.

SUMMARY OF THE INVENTION

It is an object of the invention to provide an apparatus of the above-mentioned type which is improved so that the detection of different components can be carried out with corresponding testing tubes in such a manner that the data characteristic for the measurement can automatically be considered and processed to a measurement indication.

According to a feature of the invention, the testing tube is provided with a machine-readable memory at its outer periphery which contains data which can be detected by means of a read device when the testing tube is introduced into the receiver of the air-pumping device with this data being conducted to the evaluation unit.

All data are contained in a coded manner on the readable memory which are necessary to characterize the measurement operation. These data include the following: the measurement sensitivity of the testing tube, concentration indicated in ppm, the sample quantity to be pumped which is necessary for the investigation, conversion factors or calibration data, identification number of the testing tube, date when the testing tube is no longer usable and similar information. With this information, it is assured that the specimen quantity necessary for the detection is pumped through the testing tube and that the testing tube sensitivity and type of gas to be detected are considered when the coloration zone is evaluated. The measurement precision can be increased by processing the calibration values. In a similar manner, the specific data with respect to the charge of collection tubes can be considered. If a testing tube is inserted in the incorrect direction, this is automatically detected and the measuring operation is not started. This can be especially advantageous when testing tubes of a different layer sequence are to be placed in a specific preferred direction. Testing tubes which are too old and wherein the expiration date is cancelled are not considered for evaluation.

The read device can comprise one or even several reading heads arranged about the periphery of the testing tube to be introduced. For example, the reading heads can be arranged so that each two adjacent reading heads are separated by an angle of 120° so that even narrow-banded data memories can be read by at least one of the reading heads without it being necessary to place the testing tube in a preferred position.

A suitable memory can be in the form of a bar code on a carrier which can be read in via a read device in the form of a reflex light barrier and can be decoded and further processed via an output unit. Such a bar code carrier can receive and hold a very large quantity of information on the smallest field and can be read in with the aid of simple reflex diodes. Bar code readers are available in the marketplace in many variations and can, for example, be obtained from the Hewlett-Packard Company under the product designation HEDS-3000.

The use of the testing tube provided with a memory is advantageous to the user in connection with the use of hand-driven bellows pumps as well as with machine-driven pumps if the receiving unit provided for the pump is equipped with a read device for the memory.

The detected data are advantageously inputted to a control unit as calibration values which fix the course of the measurement based on the data transmitted to the control unit. This assures that the measurement operation begins only after receipt of the necessary characteristic data and the air-pumping device is actuated for a sufficient length of time until the required air sample quantity has flowed through the testing tube and the calibration values are processed in the evaluation unit. This evaluation unit can either be in the housing of a hand-driven bellows pump or in the housing of a motor-driven feed pump.

It has been shown to be advantageous to provide a motor-driven transport device in the holder which transports the testing tube from its entry position to its final measuring position with the read device being a part of the transport device so that the content of the memory can be detected during the transport of the testing tube into its measuring position. In this way, a simplification of the take-up of the testing tube is provided and with the placement of the testing tube in its measuring position, it is assured that the characteristic data have been previously read in. For unfavorable or even falsely read-in data such as incorrect testing tube identification numbers or wherein the expiration date has passed, the user can be advised of this condition and the start of the measuring operation can be blocked.

A preferred embodiment of the transport arrangement can be provided in that a transport head is provided in which the testing tube is transported by a pair of rollers over the read head into the receiver for connection to the air-pumping unit with the roller pair being driven by a step motor. The testing tube opened at both ends must then only be introduced into the transport head thereby causing the step motor to be switched on via appropriate light barriers or contact switches so that the testing tube can be grasped by the roller pair and transported to the connection at the air-pumping device.

In order to carry out a test to determine if the air-pumping device and the feed line connected thereto are seal-tight, it is advantageous to provide the receiver with a connecting opening which can be cleared via a closure. Before the testing tube is introduced, a test for determining the sealing tightness can be carried out and, after a successful conclusion, the testing tube introduced via the transport device can clear the closure.

After the measuring operation is ended, it is advantageous for a further automation that the test tube can be removed from its receiver with the aid of the same transport device with the coloration zone which had been produced being guided past the read device for detecting the measurement data. After conclusion of the measuring operation, the evaluation unit then receives a signal by means of which, on the one hand, the transport device can be activated for removing the testing tube and, on the other hand, the read device can be activated for detecting the coloration zone. The read head then detects the length of the coloration zone precisely in the same manner as the bar code via a remission of the reflex diode. This reflection signal can be processed in the evaluation unit with the aid of the characteristic data for computing the component quantity to be detected or its concentration. With an arrangement of one read unit in the form of an arrangement of several read heads, the measurement precision can be increased by detecting the coloration zone by means of a mean value formation from the individual measurements.

An advantageous expansion of the evaluation unit is achieved by providing a calibration memory therein which holds several digitally-coded calibration values according to different types of gas. These calibration values together with the measuring data in the read unit are fed to a gas-type memory from which the measurement values specific for a particular type of gas are supplied to the display unit. In the gas-type memory, the measurement data detected at different points of time are received and can be called up therefrom via the display unit. In this way, time profiles specific to a particular type of gas are possible for the course of measured gas concentration or also for quantities of pollutants. Different gas-type profiles can be called up at specific points in time. In this way it is possible to detect the course of a gas-type measurement as a function of time as well as the composition of a gas at a fixed point in time.

A method for detecting gaseous components in air can include the steps of: pumping a sample quantity through a colorimetric testing tube by means of an air-pumping device and detecting the resulting coloration zone of the indicator by means of an evaluation unit. According to a feature of the method of the invention, the testing tube is transported via a transporting unit into a receiver for connection to the air-pumping device. A machine-readable memory is provided on the testing tube and is passed over a read unit which transmits the read-in data to a control unit. Thereafter, the air-pumping unit pumps a pregiven feed volume through the testing tube in correspondence to the read-in data whereby a coloration of the indicator is produced by the air component which is to be detected. After the coloration is concluded, the testing tube is removed from its receiver via the transport unit and moved past a read unit. The read unit scans the coloration zone and the air component determined therefrom is displayed on a display unit in accordance with type and quantity. A method of this kind makes an automatic taking of a sample reliable wherein the data of the testing tube characteristic for the measurement and of the gas component to be detected are automatically considered.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
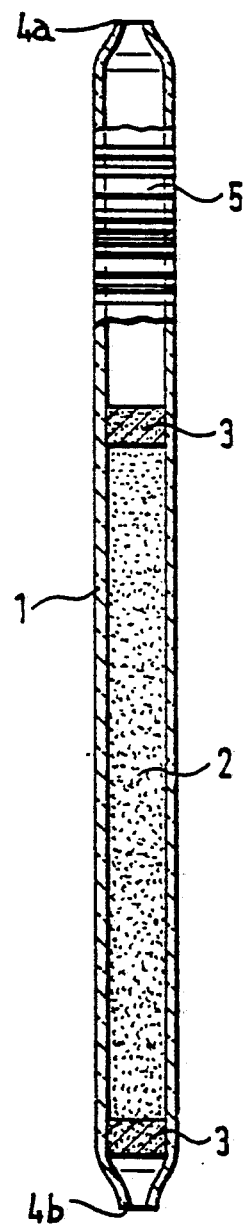
FIG. 1 is a testing tube with a bar code applied thereto.

In FIG. 1, a testing tube 1 is shown which contains a charge 2 impregnated with an indicator. The charge 2 is accommodated between porous holders 3. The two ends (4a and 4b) of the testing tube made of glass are broken off so that the charge 2 is accessible for the entry of the gas to be detected. A bar code on a badge-like carrier is provided at the outer periphery of the testing tube 1 and is in the form of a data store 5 which can be read by machine.

Figure 2:
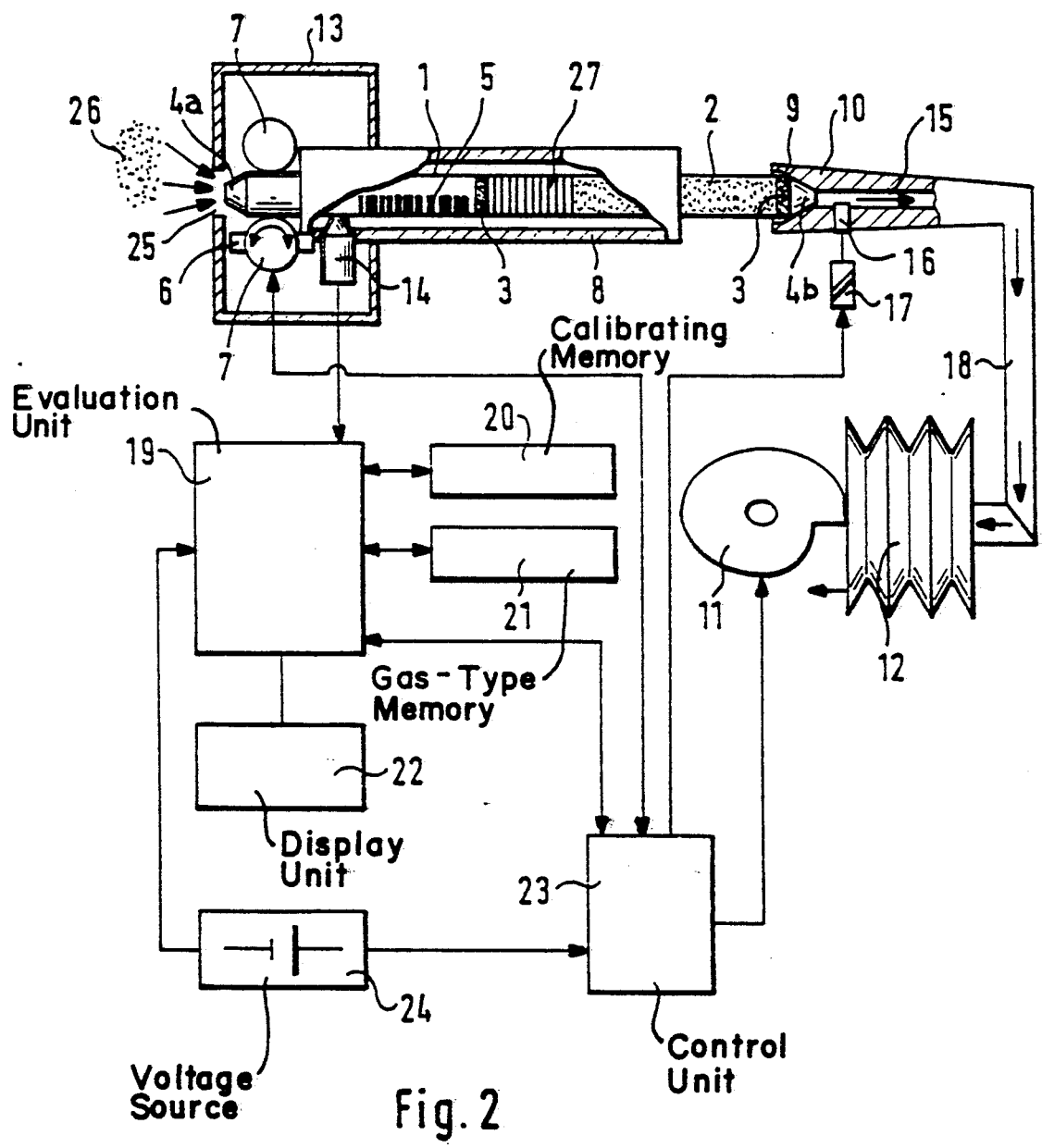
FIG. 2 is a block diagram of the apparatus according to the invention for detecting gaseous components in air.

In FIG. 2, the testing tube 1 is pushed into a holder 8 with the aid of a pair of rollers 7 driven by a step motor 6. The roller pair 7 and the step motor 6 are mounted in a transport head 13. The one end 4b of the testing tube 1 is received by a receiver 9 of the connection 10 of an air-pumping device (11, 12). The other end 4a of the testing tube 1 projects with its broken-off end into the ambient and is held by the roller pair 7 and the step motor 6. An optical reflex sensor of the read unit 14 is shown in the transport head 13. The bar code carrier 5 is led past this read unit 14. The receiver 9 has a connector opening 15 which can be opened or closed by a slide 16 which is driven by a magnetic coil 17. The connector opening 15 clears the path for the connector line 18 to the air-pumping device which can be configured as an elastic folding bellows 12. The elastic folding bellows 12 can be actuated to carry out stroke movements via an eccentric disc 11.

The evaluation of signals transmitted from the read unit 14 is performed by an evaluation unit 19 which, in turn, is connected to a calibrating memory 20 and a gas-type memory 21. The measurement values determined by the evaluation unit 19 are displayed on the display unit 22. The step motor 6, the drive of the eccentric disc 11 and the magnetic coil 17 are all connected to a control unit 23. A voltage source 24 supplies the entire apparatus with the necessary electrical energy.

For carrying out a measurement, the testing tube 1 opened at its ends is pushed into the inlet opening 25 of the transport head 13 and grasped by the roller pair 7 with the step motor 6. An electrical contact (not shown) actuates the step motor 6 whereby the testing tube is transported through the holder 8 and into the receiver 9. At the same time, the moving step motor 6 signals to the control unit 23 that a testing tube 1 has been inserted for investigation whereby the slide 16 clears the connector opening 15. During the introduction of the testing tube 1 into the receiver 9, the bar code carrier 5 is moved past the read unit 14 whereby the coded data is received by the evaluation unit 19 and the corresponding calibration values and the appropriate type of gas are called up in the calibrating memory 20 and in the gas-type memory 21.

The control unit 23 stops the step motor 6 as soon as the length of the testing tube has passed through the roller pair 7. At the same time, the eccentric drive 11 is actuated by the control unit 23 whereby the folding bellows 12 is caused to undergo a periodic stroke movement in order to pump a sample quantity 26 through the testing tube 1 and the connecting line 18 to the ambient with the pumping quantity being the quantity required according to the testing tube specification. The flow direction is indicated by appropriate flow arrows at the sample quantity 26, the connector opening 15, the connector line 18 and the folding bellows 12.

With the pumping action, a coloration zone 27 develops in the charge 2 of the testing tube 1. The testing tube 1 is then transported rearwardly out of the inlet opening 25 by the step motor 6 with the reading unit 14 registering the length of the coloration zone 27. The evaluation unit 19 is switched at this point in time by the control unit 23 so that a signal corresponding to the length of the coloration zone 27 is received and corrected with the calibration values of the calibration memory 20 corresponding thereto and is compared to the type of gas stored in the gas-type memory 21 and the measurement value processed in correspondence thereto is displayed on the display unit 22.

It is understood that the foregoing description is that of the preferred embodiments of the invention and that various changes and modifications may be made thereto without departing from the spirit and scope of the invention as defined in the appended claims.

What is claimed is:

1. An apparatus for making a measurement of a gaseous component in air with a testing tube having openable ends and containing a charge responsive to the component, the apparatus comprising:
   transport means for transporting a testing tube with both ends opened between a first position and a second position;
   machine-readable memory means arranged on said testing tube for holding stored data pertaining to the measurement to be made;
   read means for reading said stored data as the testing tube moves between said first and second positions and for scanning said testing tue and said charge to obtain measurement data with respect to the gaseous component detected;
   an air pumping device including: a receiver for receiving one of the ends of the testing tube when said testing tube is moved into said second position; and, pumping means operatively connected to said receiver for taking a sample of air through said testing tube while in said second position;
   evaluation means for receiving said stored data from said read means and processing said stored data together with said measurement data obtained by scanning said testing tube; and,
   control means connected to said evaluation means for controlling the taking of the sample via said pump means in correspondence to said data.

2. The apparatus of claim 1, said memory means being a bar code carrier mounted on the testing tube for holding said stored data in form of a bar code; and, said read means including a reflex light barrier for reading the bar code of said bar code carrier and transmitting said stored data to said evaluation unit for processing.

3. The apparatus of claim 2, comprising a control unit connected to said evaluation unit and said air pumping device; and, wherein said data from said bar code are processed as an input for said air pumping device and said evaluation unit for carrying out the detection of the gaseous component.

4. The apparatus of claim 3, said transport means comprising a holder assembly; a transporting device mounted on said holder assembly for transporting the testing tube from said first position at which the testing tube is introduced into said transporting device to said second position at which the detection is carried out; said control unit being connected to said transporting device for actuating the latter to transport the testing tube between said first and second positions; and, said read means being mounted on said holder assembly so as to permit said bar code to be read by said read means during the transport of the testing tube from said first position to said second position.

5. The apparatus of claim 4, said holder assembly comprising a holder for accommodating the testing tube in its movement between said first and second positions; and, a transport head mounted on said holder; said transporting device being mounted in said transport head and including a pair of rollers and a step motor for driving said rollers in response to a drive signal from said control unit thereby causing the testing tube to be transported over and past said read means and into said receiver thereby connecting the testing tube to said pumping means.

6. The apparatus of claim 3, said air pumping device comprising; conduit means interconnecting said receiver and said pumping means; and, a closure actuable by said control unit for opening and closing said conduit means.

7. The apparatus of claim 1, wherein said testing tube is a colorimetric testing tube in which a coloration zone appears in the charge when the sample of air is pumped through the testing tube when said testing tube is in said second position; and, the coloration zone is scanned by said read means during a transport of the testing tube from said second position to said first position.

8. The apparatus of claim 1, said evaluation unit comprising: a calibration memory containing a plurality of digitally-coded calibration values which are different according to the gaseous component; a gas memory; and, a display unit; and, wherein said calibration values together with said data from said read means taken for separate measurements at different times are supplied to said gas memory for forming measuring values which are transmitted to said display unit and which are specific to the gaseous component detected.

9. A method of detecting of gaseous component in air the method comprising the steps of: with providing a colorimetric testing tube having openable ends and containing a charge responsive to the component by forming a coloration zone:

inserting the testing tube with both ends open into a transport device for transporting the testing tube between a first position and a second position, the testing tube having a machine-readable memory formed thereon for storing data pertaining to the measurement to be made;

transporting the testing tue from the first position to the second position;

reading said data by means of a read device as said testing tube is moved from said first position to said second position and transmitting said data into an evaluation unit;

actuating a pumping device by means of a control unit in correspondence to the data read into said evaluation unit while the testing tube is in said second position thereby pumping a sample of air through the testing tube to cause a coloration zone to develop in the charge contained in the testing tube;

after the coloration zone is formed, transporting the testing tube from the second position back to the first position;

scanning the coloration zone with the read device as the testing tube is transported back into the first position from the second position to obtain measurement data;

transmitting the measurement data from the coloration zone into said evaluation unit wherein the measurement data is evaluated to determine the gaseous component in accordance with the type of component and quantity; and displaying the type of component and quantity on a display unit.

* * * * *

UNITED STATES PATENT AND TRADEMARK OFFICE
CERTIFICATE OF CORRECTION

PATENT NO. : 5,069,879

DATED : December 3, 1991

INVENTOR(S) : Kurt Leichnitz, Wolfgang May, Wolfgang Bäther and Wolfgang Evers

It is certified that error appears in the above-identified patent and that said Letters Patent is hereby corrected as shown below:

In column 5, line 58: delete "tue" and substitute -- tube -- therefor.

In column 6, line 43: delete ";" and substitute -- : -- therefor.

In column 6, line 65: delete "with".

In column 6, line 68: delete ":" and substitute -- ; -- therefor.

In column 7, line 7: delete "tue" and substitute -- tube -- therefor.

Signed and Sealed this

Sixteenth Day of March, 1993

Attest:

STEPHEN G. KUNIN

Attesting Officer

Acting Commissioner of Patents and Trademarks